US011953503B2

United States Patent
Althaus et al.

(10) Patent No.: US 11,953,503 B2
(45) Date of Patent: Apr. 9, 2024

(54) METHOD FOR QUANTITATIVELY DETERMINING A THERAPEUTIC TNF-ALPHA INHIBITOR

(71) Applicant: Siemens Healthcare Diagnostics Products GmbH, Marburg (DE)

(72) Inventors: Harald Althaus, Wetter (DE); Thorsten Keller, Rauschenberg (DE)

(73) Assignee: Siemens Healthcare Diagnostics Products GmbH, Marburg (DE)

( * ) Notice: Subject to any disclaimer, the term of this patent is extended or adjusted under 35 U.S.C. 154(b) by 434 days.

(21) Appl. No.: 16/962,566

(22) PCT Filed: Jan. 14, 2019

(86) PCT No.: PCT/EP2019/050760
§ 371 (c)(1),
(2) Date: Jul. 16, 2020

(87) PCT Pub. No.: WO2019/141614
PCT Pub. Date: Jul. 25, 2019

(65) Prior Publication Data
US 2020/0400681 A1    Dec. 24, 2020

(30) Foreign Application Priority Data

Jan. 17, 2018  (EP) .................... 18152009

(51) Int. Cl.
*G01N 33/68*    (2006.01)
*G01N 33/543*   (2006.01)

(52) U.S. Cl.
CPC ..... *G01N 33/6863* (2013.01); *G01N 33/5434* (2013.01); *G01N 2333/525* (2013.01)

(58) Field of Classification Search
None
See application file for complete search history.

(56) References Cited

U.S. PATENT DOCUMENTS

| 3,996,345 A | 12/1976 | Ullman et al. |
| 6,090,382 A * | 7/2000 | Salfeld .................. A61P 31/22 530/387.3 |
| 8,574,855 B2 * | 11/2013 | Singh .................. A61P 25/00 435/7.1 |
| 2005/0176808 A1 | 8/2005 | Najib et al. |
| 2012/0171697 A1 | 7/2012 | Kappel et al. |
| 2018/0003719 A1 | 1/2018 | Warthoe |

FOREIGN PATENT DOCUMENTS

| CN | 107110853 A | 6/2017 |
| EP | 0515194 * | 11/1992 |
| EP | 0515194 A2 | 11/1992 |
| WO | 9506877 A1 | 3/1995 |
| WO | 98/11918 A1 | 3/1998 |
| WO | 2009032128 A1 | 3/2009 |
| WO | 2015108907 A2 | 7/2015 |
| WO | 2016110595 A1 | 7/2016 |
| WO | 2018007327 A1 | 1/2018 |

OTHER PUBLICATIONS

Udenfriend, S. et al., Scintillation proximity radioimmunoassay utilizing 125-I-labelled ligands, Proc. Natl. Acad. Sci. USA 1985, 82, 8672-8676; 1985.
Peula, J.M. et al., Covalent coupling of antibodies to aldehyde groups on polymer carriers. Journal of Materials Science: Materials in Medicine 1995; 6: 779-785.; 1995.
Newman, D.J. et al., Particle enhanced light scattering immunoassay. Ann Clin Biochem 1992; 29: 22-42.; 1992.
Finckh et al.,: "Influence of anti-infliximab antibodies and residual infliximab concentrations on the occurrence of acquired drug resistance to infliximab in rheumatoid arthritis patients"; Joint Bone Spine, Elsevier, Amsterdam, NL, Bd. 77, Nr. 4, 1. Jul. 2010 (Jul. 1, 2010), pp. 313-318; XP027135651; ISSN: 1297-319X; 2010.

\* cited by examiner

*Primary Examiner* — Brian Gangle
*Assistant Examiner* — Andrea K McCollum
(74) *Attorney, Agent, or Firm* — BakerHostetler

(57) ABSTRACT

Provided is a universal method for quantitatively determining therapeutic tumor necrosis factor (TNF)-alpha inhibitors in patient samples that is sufficiently sensitive for being able to detect all therapeutic TNF-alpha inhibitors.

9 Claims, No Drawings

METHOD FOR QUANTITATIVELY DETERMINING A THERAPEUTIC TNF-ALPHA INHIBITOR

CROSS-REFERENCE TO RELATED APPLICATIONS

This application is a 35 U.S.C. § 371 national phase application of International Patent Application No. PCT/EP2019/050760 filed Jan. 14, 2019, which claims priority to European application No. 18152009.9, filed Jan. 17, 2018, the entire disclosure of each of which is incorporated herein by reference in its entirety.

The invention is in the field of in vitro diagnostics and relates to a method for quantitatively determining therapeutic TNF-alpha inhibitors.

Inhibitors of the tumor necrosis factor alpha protein (TNF-alpha, TNF-a, cachectin) are used as drugs for treating inflammatory diseases, such as, for example, Crohn's disease, Bechterew's disease, psoriasis and particularly rheumatoid arthritis. TNF-alpha inhibitors are TNF-alpha-binding proteins, such as, for example, anti-TNF-alpha antibodies or fragments thereof or fusion proteins produced by gene technology that comprise the extracellular TNF-alpha-binding domain of the human TNF receptor. All therapeutically effective TNF-alpha inhibitors bind to TNF-alpha protein and bring about an inactivation of the TNF-alpha protein by preventing the binding of TNF-alpha protein to the TNF receptors.

Various TNF-alpha inhibitors have been authorized for the therapy of chronic inflammatory diseases, such as, for example, infliximab, etanercept, adalimumab, certolizumab pegol or golimumab and various biosimilars (biopharmaceutical imitation products).

One problem is that not all patients respond equally to TNF-alpha inhibitors. It is known that the serum or plasma concentration of TNF-alpha inhibitors distinctly correlates with the clinical symptoms of the patients treated. The efficacy of a TNF-alpha inhibitor therapy generally correlates with the amount of therapeutic antibody that is detectable in the serum or plasma of the patient just before the next drug administration, the so-called trough level.

Individual differences in pharmacokinetics and the appearance of antibodies against the therapeutic TNF-alpha inhibitor (so-called ADA's or anti-drug antibodies) can influence the trough level and hence the efficacy of a TNF-alpha inhibitor therapy. The absence of success in therapy can have different causes, such as, for example, an underdosage or the presence of anti-drug antibodies.

Thus, in order to be able to optimally shape a TNF-alpha inhibitor therapy, for example by an alteration of the dosage or by a switch to another preparation, it is necessary to establish the serum or plasma concentration of the therapeutic TNF-alpha inhibitor in a treated patient.

Different methods for quantitatively determining therapeutic TNF-alpha inhibitors in patient samples are known. Firstly, commercial ELISA assays for determination of specific TNF-alpha inhibitors are known, in which monoclonal antibodies specific for the particular TNF-alpha inhibitor are fixed on a microtiter plate (IDKmonitor® assays for adalimumab, infliximab and etanercept, Immundiagnostik AG, Bensheim, Germany) or in which TNF-alpha protein is directly or indirectly fixed on a microtiter plate (IDKmonitor® assay for golimumab, Immundiagnostik AG, Bensheim, Germany, and level adalimumab and level infliximab assays from Sanquin, Amsterdam, the Netherlands).

WO-A1-2016/110595 and WO-A1-2018/007327 disclose particle-enhanced, turbidimetric methods for quantitatively determining therapeutic TNF-alpha inhibitors in patient samples, in which polystyrene particles coated with TNF-alpha protein are mixed with the sample and agglutination in the reaction mixture is measured. One advantage is that what is concerned is a universal assay design, by means of which any therapeutic TNF-alpha inhibitor is detectable. For a precise quantification of a specific TNF-alpha inhibitor, only a calibration curve prepared with the same specific TNF-alpha inhibitor is required. However, one disadvantage is that the use of a nonspecific, TNF-alpha inhibitor-crosslinking ligand from the group consisting of anti-Ig antibodies (e.g., Fc- or Fab-specific antibodies), protein G, protein A, protein H, protein L and protein A/G fusion protein is additionally required in order to achieve a sufficient sensitivity of the assay, so that all therapeutic TNF-alpha inhibitors, particularly also etanercept (brand name ENBREL® (etanercept), Pfizer), are detectable.

The problem addressed by the present invention was therefore that of providing a universal method for quantitatively determining therapeutic TNF-alpha inhibitors in patient samples that is sufficiently sensitive for being able to detect all therapeutic TNF-alpha inhibitors.

In relation to the known particle-enhanced method, the problem addressed by the present invention was particularly that of providing a universal, particle-enhanced method for quantitatively determining therapeutic TNF-alpha inhibitors in patient samples that is sufficiently sensitive for being able to detect all therapeutic TNF-alpha inhibitors without the need to use a nonspecific, TNF-alpha inhibitor-crosslinking ligand.

It was found that contacting the sample with isolated, free TNF-alpha protein and the subsequent addition of a TNF-alpha binding partner achieve a sufficiently sensitive method for quantitatively determining therapeutic TNF-alpha inhibitors, by means of which all therapeutic TNF-alpha inhibitors are detectable. The therapeutic TNF-alpha inhibitor present in the sample binds to the added TNF-alpha protein and thereby prevents the binding of the subsequently added TNF-alpha binding partner. The greater the amount of a therapeutic TNF-alpha inhibitor present in a sample, the stronger its inhibition of the formation of a complex composed of TNF-alpha protein and the added TNF-alpha binding partner. What is thus essentially concerned is a competitive assay method.

In relation to particle-enhanced methods, it was found in particular that contacting the sample with isolated, free TNF-alpha protein and the subsequent addition of a particulate solid phase coated with a TNF-alpha binding partner achieve a sufficiently sensitive method for quantitatively determining therapeutic TNF-alpha inhibitors, by means of which all therapeutic TNF-alpha inhibitors are detectable without the need to use a nonspecific, TNF-alpha inhibitor-crosslinking ligand. The therapeutic TNF-alpha inhibitor present in the sample binds to the added TNF-alpha protein and thereby prevents the binding of the subsequently added solid phase-coupled TNF-alpha binding partner. The greater the amount of a therapeutic TNF-alpha inhibitor present in a sample, the stronger its inhibition of the agglutination reaction.

The present invention thus provides a method for quantitatively determining a therapeutic TNF-alpha inhibitor in a sample. The method comprises the following steps:
a) providing a reaction mixture by contacting the sample
  i. with isolated, free TNF-alpha protein and then
  ii. with a first TNF-alpha binding partner;

b) determining the amount of a complex which forms in the reaction mixture and is composed of TNF-alpha protein and the first TNF-alpha binding partner; and then c) determining the amount of the therapeutic TNF-alpha inhibitor in the sample by comparing the thus determined amount of the complex composed of TNF-alpha protein and the first TNF-alpha binding partner in the reaction mixture with amounts of a complex composed of TNF-alpha protein and the first TNF-alpha binding partner in reaction mixtures containing samples having known concentrations of a TNF-alpha binding partner.

The sample can be a body fluid sample, preferably a human body fluid sample, such as, for example, whole blood, plasma, serum or urine. Usually, the body fluid sample comes from a patient to whom a therapeutic TNF-alpha inhibitor has been administered.

The method is suitable for quantitatively determining therapeutic TNF-alpha inhibitors which bind to TNF-alpha protein, such as, for example, anti-TNF-alpha antibodies or fragments thereof or fusion proteins produced by gene technology that comprise the extracellular TNF-alpha binding domain of the human TNF receptor. All therapeutically effective TNF-alpha inhibitors bind to TNF-alpha protein and bring about an inactivation of the TNF-alpha protein by preventing the binding of TNF-alpha protein to the TNF receptors. The method is particularly suitable for quantitatively determining therapeutic TNF-alpha inhibitors from the group consisting of infliximab, etanercept, adalimumab, certolizumab pegol and golimumab and also biosimilars thereof.

The isolated, free TNF-alpha protein can be recombinantly or synthetically produced TNF-alpha protein or a native TNF-alpha protein, i.e., it can come from natural sources, for example TNF-alpha protein purified from human blood. Suitable for producing recombinant TNF-alpha protein are known prokaryotic or eukaryotic expression systems, such as, for example, expression in bacteria (e.g., *E. coli*), in yeasts (e.g., *Saccharomyces cerevisiae, Pichia pastoris*), in plant, animal or human cell cultures (e.g., HEK cells). Suitable for producing synthetic TNF-alpha protein are known techniques for in vitro protein synthesis, such as, for example, solid-phase synthesis (e.g., Merrifield synthesis).

The TNF-alpha protein is preferably human TNF-alpha protein. The term "TNF-alpha protein" encompasses not only the complete TNF-alpha protein, but also fragments of the complete TNF-alpha protein, to which therapeutic TNF-alpha inhibitors can bind. The term "TNF-alpha protein" furthermore encompasses not only the wild-type TNF-alpha protein or fragments thereof, but also TNF-alpha proteins having one or more amino acid substitutions, to which therapeutic TNF-alpha inhibitors can bind. The N-terminus of the TNF-alpha protein or of a TNF-alpha protein fragment can be fused with a heterologous signal sequence, i.e., with a polypeptide which is usually not present in the human TNF-alpha protein, but which positively affects the expression and/or secretion of the recombinantly expressed TNF-alpha protein in the chosen expression system. Furthermore, the C-terminus of the TNF-alpha protein or of a TNF-alpha protein fragment can be fused with one or more affinity tags which allow the binding of the, for example, recombinantly expressed protein to an affinity support, this allowing, for example, the purification of recombinantly expressed TNF-alpha protein. Preference is given to small affinity tags having a length of not more than 12 amino acids. Particular preference is given to affinity tags from the group consisting of His-tag, Flag-tag, Arg-tag, c-Myc-tag and Strep-tag. Suitable affinity supports which bind with high affinity to an affinity tag are, for example, specific antibodies, immobilized cations (e.g., $Ni^{2+}$ with affinity for His-tags) or other types of binding partners (e.g., streptavidin with affinity for Strep-tags). The term "isolated, free TNF-alpha protein" refers to an unbound, unconjugated TNF-alpha protein which, for example, is not associated with a binding partner or with a solid phase or with a detectable label or with a component of a signal-forming system.

After the sample has been mixed or contacted with isolated, free TNF-alpha protein, the reaction mixture is preferably first incubated for a period of from 1 second to 10 minutes, particularly preferably for a period of from 5 seconds to 5 minutes, before the first TNF-alpha binding partner is then added. Preferably, the reaction mixture is incubated at a temperature of about 37° C. This ensures that all the molecules of a therapeutic TNF-alpha inhibitor present in the sample bind to the added free TNF-alpha protein and thereby increases the precision of the quantitative determination.

In a preferred embodiment of the method according to the invention, the first TNF-alpha binding partner is associated with a particulate solid phase, and the agglutination of the particulate solid phase in the reaction mixture is measured in order to determine the amount of the complex which forms in the reaction mixture and is composed of TNF-alpha protein and the first TNF-alpha binding partner.

The term "particulate solid phase" is to be understood in the context of this invention to mean noncellular particles having an approximate diameter of at least 20 nm and not more than 20 µm, usually between 200 nm and 350 nm, preferably between 250 and 320 nm, particularly preferably between 270 and 290 nm, very particularly preferably 280 nm. The microparticles can have a regular or irregular shape. They can be spheres, spheroids, spheres having more or less large cavities or pores. The microparticles can consist of organic material, of inorganic material or of a mixture or a combination of the two. They can consist of a porous or nonporous, swellable or nonswellable material. In principle, the microparticles can have any density, but preference is given to particles having a density which comes close to the density of water, such as about 0.7 to about 1.5 g/ml. The preferred microparticles are suspendable in aqueous solutions and suspension-stable for as long as possible. They may be transparent, semitransparent or nontransparent. The microparticles can consist of multiple layers, such as, for example, the so-called "core-and-shell" particles with one core and one or more enveloping layers. The term microparticles encompasses, for example, dye crystals, metal sols, silica particles, glass particles and magnetic particles. Preferred microparticles are particles which are suspendable in aqueous solutions and consist of water-insoluble polymer material, particularly of substituted polyethylenes. Very particular preference is given to latex particles, for example composed of polystyrene, acrylic acid polymers, methacrylic acid polymers, acrylonitrile polymers, acrylonitrile butadiene styrene, polyvinyl acetate acrylate, polyvinyl pyridine, vinyl chloride acrylate. Of particular interest are latex particles having reactive groups on their surface, such as, for example, carboxyl, amino or aldehyde groups which allow covalent bonding of an anti-TNF-alpha binding partner to the latex particles. Human, animal, plant or fungal cells or bacteria are explicitly not encompassed by the term "particulate solid phase" in the context of this invention.

The term "associated" is to be understood broadly and encompasses, for example, covalent and noncovalent bonding, direct and indirect binding, adsorption to a surface and entrapment in an indentation or a cavity, etc. In the case of covalent bonding, the antibodies are bound to the solid phase or to a component of a signal-giving system via a chemical bond. Examples of noncovalent bonding are surface adsorption, entrapment in cavities or the binding of two specific binding partners. Besides direct binding to the solid phase or the component of a signal-giving system, the antibodies can also be indirectly bound to the solid phase or the label via a specific interaction with other specific binding partners. A detailed illustration of this shall be given using examples: the biotinylated antibody can be bound to the label via label-bound avidin, or a fluorescein-antibody conjugate can be bound to the solid phase via solid phase-bound anti-fluorescein antibodies, or the antibody can be bound to the solid phase or the label via immunoglobulin-binding proteins.

The TNF-alpha binding partner with which the particulate solid phase is coated can be an anti-TNF-alpha antibody, a peptide or nucleic acid aptamer or a peptide affimer.

The anti-TNF-alpha antibody with which the particulate solid phase is coated is an immunoglobulin, for example an immunoglobulin of the class or subclass IgA, IgD, IgE, $IgG_1$, $IgG_{2a}$, $IgG_{2b}$, $IgG_3$, $IgG_4$, IgM. The antibody has at least one binding site (commonly called a paratope) for an epitope (also commonly called an antigenic determinant) in the TNF-alpha protein. Such an epitope is, for example, characterized by its spatial structure and/or by the presence of polar and/or apolar groups. The binding site of the antibody is complementary to the epitope. The antigen-antibody reaction works according to the so-called "key-and-lock principle" and is generally specific to a high degree, i.e., the antibodies are able to distinguish small deviations in the primary structure, in the charge, in the spatial configuration and the steric arrangement of the TNF-alpha protein.

The term "antibody" is to be understood in the context of this invention to mean, however, not only complete antibodies, but expressly also antibody fragments, such as, for example, Fab, Fv, $F(ab')_2$, Fab'; and also chimeric, humanized, bi- or oligospecific or "single-chain" antibodies; additionally also aggregates, polymers and conjugates of immunoglobulins and/or the fragments thereof, provided that the properties of binding to the TNF-alpha protein are maintained. Antibody fragments can, for example, be produced by enzymatic cleavage of antibodies using enzymes such as pepsin or papain. Antibody aggregates, polymers and conjugates can be generated by various methods, for example by heat treatment, conversion with substances such as glutaraldehyde, reaction with immunoglobulin-binding molecules, biotinylation of antibodies and subsequent reaction with streptavidin or avidin, etc.

An anti-TNF-alpha antibody in the context of this invention can be a monoclonal antibody or a polyclonal antibody. The antibody can have been produced by customary methods, for example by immunizing an animal, such as, for example, mouse, rat, guinea pig, rabbit, horse, donkey, sheep, goat, chicken, etc., with TNF-alpha protein and subsequently obtaining the antiserum; or by establishing hybridoma cells and subsequently purifying the secreted antibodies; or by cloning and expressing the nucleotide sequences or modified versions thereof that encode the amino acid sequences responsible for the binding of the natural antibody to the TNF-alpha protein.

If a therapeutic TNF-alpha inhibitor is present in the sample, said inhibitor binds to the added free TNF-alpha protein in the reaction mixture and thereby prevents the binding of the subsequently added solid phase-coupled TNF-alpha binding partner, i.e., the formation of a complex composed of TNF-alpha protein and solid phase-coupled TNF-alpha binding partner. Only free, unbound TNF-alpha protein is now still bound by the solid phase-coupled TNF-alpha binding partner and brings about an agglutination of the particulate solid phase in the reaction mixture. The greater the amount of a therapeutic TNF-alpha inhibitor present in a sample, the stronger its inhibition of the formation of a complex composed of TNF-alpha protein and solid phase-coupled TNF-alpha binding partner, i.e., the agglutination reaction.

The agglutination of the particulate solid phase in the reaction mixture can be measured photometrically, for example turbidimetrically or nephelometrically. Binding assays based on the principle of particle-enhanced light scattering have been known since about 1920 (for an overview, see Newman, D. J. et al., Particle enhanced light scattering immunoassay. Ann Clin Biochem 1992; 29: 22-42). Preferably, polystyrene particles having a diameter of from 0.1 to 0.5 µm, particularly preferably having a diameter of from 0.15 to 0.35 µm, are used in this connection. Preferably, polystyrene particles having amine, carboxyl or aldehyde functions are used. Further preferably, shell/core particles are used. The synthesis of the particles and the covalent coupling of ligands is, for example, described in Peula, J. M. et al., Covalent coupling of antibodies to aldehyde groups on polymer carriers. Journal of Materials Science: Materials in Medicine 1995; 6: 779-785.

Alternatively, the measurement of the agglutination of the particulate solid phase in the reaction mixture can be measured by the measurement of a signal which is generated by a signal-forming system when a first and a second component of the signal-forming system are brought into close proximity to one another. In this connection, a first fraction of the particulate solid phase is associated with a first component of a signal-forming system and a second fraction of the particulate solid phase is associated with a second component of the signal-forming system, the first and second component of the signal-forming system cooperating such that a detectable signal forms when the first and the second component of the signal-forming system are brought into close proximity to one another and the agglutination of the particulate solid phase in the reaction mixture being measured on the basis of the signal formed.

In this embodiment of the method according to the invention, the signal-forming system comprises at least one first and one second component which cooperate such that a detectable signal forms when they are brought into close proximity to one another and can interact with one another as a result. An interaction between the components is to be understood to mean particularly an energy transfer—i.e., the direct transfer of energy between the components, for example by light or electron radiation and also via reactive chemical molecules, such as, for example, transient single oxygen. The energy transfer can take place from one component to another, but a cascade of various substances via which the energy transfer flows is also possible. For example, the components can be a pair composed of an energy donor and an energy receiver, such as, for example, photosensitizer and chemiluminescent agent (EP-A2-0515194, LOCI® technology) or photosensitizer and fluorophore (WO or radioactive iodine<125> and fluorophore (Udenfriend et al. (1985) Proc. Natl. Acad. Sci. 82: 8672-8676) or fluorophore and fluorescence quencher (U.S. Pat. No. 3,996,345). Particularly preferably, the first component of the signal-forming system is a chemiluminescent agent and the second component of the signal-forming system is a photosensitizer, or vice versa, and the chemiluminescence in the reaction mixture is measured.

After the agglutination in the reaction mixture has been measured (e.g., by determination of the maximum absorption change in the reaction mixture), the thus measured agglutination is compared with the agglutination in reaction mixtures containing samples having known concentrations of a TNF-alpha binding partner. To this end, samples having different known concentrations of a therapeutic TNF-alpha inhibitor, of an anti-TNF-alpha antibody, of a TNF-alpha-specific peptide or nucleic acid aptamer or of a TNF-alpha-specific peptide affimer (so-called calibrators) are usually measured beforehand in reaction mixtures using the same method, and what is prepared is a calibration curve at which the concentration of the tested sample can then be read off or be ascertained after a conversion step.

The above-described particle-based agglutination assays are so-called homogeneous methods, which are distinguished by the fact that no removal of unbound TNF-alpha protein or unbound solid phase-coupled TNF-alpha binding partner is required for the quantitative detection of the complex which forms in the reaction mixture and is composed of TNF-alpha protein and solid phase-coupled TNF-alpha binding partner. The amount of the complex which forms in the reaction mixture and is composed of TNF-alpha protein and solid phase-coupled TNF-alpha binding partner is measured after or even during the binding reaction without a further separation or wash step for removing unbound binding partners in the reaction mixture.

Other embodiments of the method according to the invention are so-called heterogenous methods, which are distinguished by the fact that a removal of unbound TNF-alpha protein and unbound solid phase-coupled TNF-alpha binding partner is required for the quantitative detection of the complex which forms in the reaction mixture and is composed of TNF-alpha protein and solid phase-coupled TNF-alpha binding partner. The amount of the complex which forms in the reaction mixture and is composed of TNF-alpha protein and solid phase-coupled TNF-alpha binding partner is only measured after removal of the complex from the other constituents of the reaction mixture. For the removal of the complex, one or more separation and/or wash steps are carried out with the solid phase to which the complex is bound. Thereafter, the solid phase is contacted with one or more reagents for the quantitative detection of the complex.

Thus, in a further embodiment of the method according to the invention, the first TNF-alpha binding partner is associated with a solid phase, and the amount of the complex which forms in the reaction mixture and is composed of TNF-alpha protein and the first TNF-alpha binding partner in the reaction mixture is determined in step b) by removing the reaction mixture from the solid phase. This is followed by contacting the solid phase with a second TNF-alpha binding partner and measuring the amount of the second TNF-alpha binding partner which is bound to the complex which was formed in the reaction mixture and is associated with the solid phase and is composed of TNF-alpha protein and the first TNF-alpha binding partner.

The solid phase with which the first TNF-alpha binding partner is associated can be a particulate solid phase as already described further above. The solid phase can, however, also consist of the materials as already described further above for the particulate solid phase, but have other forms, such as, for example, the form of a vessel, tube, microtitration plate, bead, rod, strip, filter or chromatography paper, etc.

The second TNF-alpha binding partner which, after the removal of the solid phase, is contacted with the solid phase for the quantitative determination of the amount of the complex bound to the solid phase and composed of TNF-alpha protein and first TNF-alpha binding partner is preferably associated with a component of a signal-forming system.

The component of a signal-forming system can be a label which itself generates a detectable signal, meaning that no further components are necessary. Many organic molecules absorb ultraviolet and visible light, said molecules being able to come into an excited energy state as a result of energy transmitted by the light absorption and emitting the absorbed energy in the form of light of a wavelength other than that of the irradiated light. Yet other labels can directly generate a detectable signal, such as, for example, radioactive isotopes or dyes.

The component of a signal-forming system can, however, also be a label which requires further components for signal generation, such as, for example, substrates, coenzymes, quenchers, accelerators, additional enzymes, substances which react with enzyme products, catalysts, activators, cofactors, inhibitors, ions, etc. Suitable labels are, for example, enzymes including horseradish peroxidase, alkaline phosphatase, glucose-6-phosphate dehydrogenase, alcohol dehydrogenase, glucose oxidase, β-galactosidase, luciferase, urease and acetyl cholinesterase; dyes; fluorescent substances including fluorescein isothiocyanate, rhodamine, phycoerythrin, phycocyanin, ethidium bromide, 5-dimethylaminonaphthalene-1-sulfonyl chloride and fluorescent chelates of rare earths; chemiluminescent substances including luminol, isoluminol, acridinium compounds, olefin, enol ether, enamine, aryl vinyl ether, dioxene, arylimidazole, lucigenin, luciferin and aequorin; sensitizers including eosin, 9,10-dibromoanthracene, methylene blue, porphyrin, phthalocyanine, chlorophyll, rose bengal; coenzymes; enzyme substrates; radioactive isotopes including $^{125}I$, $^{131}I$, $^{14}C$, $^{3}H$, $^{32}P$, $^{35}S$, $^{14}C$, $^{51}Cr$, $^{59}Fe$, $^{57}Co$ and $^{75}Se$; particles including magnetic particles or particles, preferably latex particles, which themselves can, for example, be labeled with dyes, sensitizers, fluorescent substances, chemiluminescent substances, isotopes or other detectable labels; sol particles including gold or silver sols, etc.

The second TNF-alpha binding partner can, as already described further above for the first TNF-alpha binding partner, be an anti-TNF-alpha antibody, a peptide or nucleic acid aptamer or a peptide affimer. The first and second TNF-alpha binding partner can be the same binding partner, for example the same monoclonal anti-TNF-alpha antibody, or different binding partners can be concerned, for example a monoclonal anti-TNF-alpha antibody and a peptide aptamer or two monoclonal anti-TNF-alpha antibodies which bind to different epitopes of the TNF-alpha protein.

It was found that the method according to the invention allows the use of a single universal calibrator for determining any desired therapeutic TNF-alpha inhibitor. The universal calibrator can contain a single therapeutic TNF-alpha inhibitor, preferably from the group consisting of infliximab, etanercept, adalimumab, certolizumab pegol and golimumab and biosimilars thereof, or a mixture of at least two different therapeutic TNF-alpha inhibitors or biosimilars thereof or an anti-TNF-alpha antibody or a TNF-alpha-specific peptide or nucleic acid aptamer or a TNF-alpha-specific peptide affimer. This has the advantage that a single assay kit and a single calibrator can be used for the determination of any desired therapeutic TNF-alpha inhibitor and that the use of inhibitor-specific assay kits or calibrators can be dispensed with. A "universal calibrator" is also to be understood to mean a set of calibrator materials which merely differ with respect to the concentration of the therapeutic TNF-alpha inhibitor(s) present therein or of the anti-TNF-alpha antibody or of the TNF-alpha-specific peptide or nucleic acid aptamer or of the TNF-alpha-specific peptide affimer. Although not every combination of therapeutic TNF-alpha inhibitor to be determined and calibrator shows the same reactivity, it is possible by using linear conversion functions or polynomial conversion functions (2nd or 3rd degree) to counterbalance the different reactivities of the TNF-alpha inhibitors and to thus calculate correct concentrations.

The present invention further provides an assay kit for use in a method for quantitatively determining a therapeutic TNF-alpha inhibitor in a sample and particularly for carrying out a method according to the invention. The assay kit contains at least the following components:
   a) a first vessel containing a reagent, the reagent containing 50 µg-2 mg/L isolated, free TNF-alpha protein; and
   b) a second vessel containing a first TNF-alpha binding partner.

The reagent in the first vessel contains an isolated, free TNF-alpha protein of the kind as already described further above, particularly preferably a recombinant TNF-alpha protein. The reagent contains the TNF-alpha protein in a final concentration of 50 µg-2 mg/L, preferably of 50 µg-1 mg/L, very particularly preferably of 100 µg-0.5 mg/L. The reagent can be provided in the vessel in liquid form. Alternatively, the reagent can, for the purpose of long-term stabilization, also be provided as a lyophilisate, which is only resuspended just before use with a suitable solvent volume so that the desired final concentration is reached.

If some or all reagents of the assay kit are present as lyophilisates, the assay kit can additionally contain the solvents required for dissolving the lyophilisates, such as, for example, distilled water or suitable buffers.

The second vessel of the assay kit, which contains a first TNF-alpha binding partner, can contain the first TNF-alpha binding partner in different embodiments.

In one embodiment, the second vessel can contain a reagent which, in turn, contains a particulate solid phase, preferably latex particles, to which the first TNF-alpha binding partner is associated. The reagent can be a liquid suspension or be a resuspendable lyophilisate of same. Such an assay kit is suitable for the measurement of agglutination by means of photometric methods.

Another embodiment of the assay kit contains, in addition to the first vessel and the second vessel, furthermore a third vessel which contains a second TNF-alpha binding partner. Said third vessel of the assay kit can contain the second TNF-alpha binding partner in different embodiments. Preferably, the third vessel likewise contains a particulate solid phase which is coated with the second TNF-alpha binding partner, preferably with an anti-TNF-alpha antibody. In this connection, the particulate solid phase of the reagent in the second vessel is associated with a first component of a signal-forming system and the particulate solid phase of the reagent in the third vessel is associated with a second component of the signal-forming system, the first and second component of the signal-forming system cooperating such that a detectable signal forms when the first and the second component of the signal-forming system are brought into close proximity to one another. Preferably, the first component of the signal-forming system is a chemiluminescent agent and the second component of the signal-forming system is a photosensitizer, or vice versa. Such an assay kit is suitable for the measurement of agglutination by means of chemiluminescence measurement.

A first or second anti-TNF-alpha antibody with which the solid phase in the reagent in the second and/or the third vessel is coated is preferably a monoclonal antibody.

In another embodiment, the first TNF-alpha binding partner present in the second vessel is associated with a surface of the second vessel, for example on the base of a well of a microtiter plate or on the inner side of a reaction vessel. The term "associated" is, as already described further above, to be understood broadly in this connection. Such an assay kit is particularly suitable for carrying out heterogenous assay methods, such as, for example, ELISA assays. Such an assay kit preferably further contains a third vessel containing a second TNF-alpha binding partner, preferably in the form of a liquid reagent (or of a lyophilisate of same) containing the second TNF-alpha binding partner. Particularly preferably, the second TNF-alpha binding partner is associated with a component of a signal-forming system, as already described by way of example further above.

The following examples serve to illustrate the present invention and are not to be understood as a limitation.

EXAMPLES

Example 1: Homogeneous Agglutination Assays for Quantitatively Determining Various Therapeutic TNF-Alpha Inhibitors Reagent 1:
500 µg of human, recombinant, lyophilized TNF-alpha protein (Active Bioscience GmbH, Hamburg, Germany) were dissolved in 500 µL of water and stored at 2-8° C. (TNF-alpha stock solution, 1 mg/mL). To prepare Reagent 1, the TNF-alpha stock solution was diluted to a final concentration of 250 µg/L TNF-alpha protein in a lipoprotein-free human citrate plasma.

Reagent 2: To prepare Reagent 2, about 1.5 mg of the monoclonal anti-TNF-alpha antibody MAK 1D4 were mixed and incubated with 1 mL of polystyrene latex particles (40 mg/mL, particle diameter 0.2-0.3 µm) in a buffer solution. After repeated washing of the particles, the particles were subsequently resuspended in 60 mL of a buffer solution.

The monoclonal anti-TNF-alpha antibody MAK 1D4 was produced by immunization of a mouse with human TNF-alpha protein and subsequent establishment of hybridoma cells.

To prepare samples containing a therapeutic TNF-alpha inhibitor, different amounts of
   adalimumab (HUMIRAO (adalimumab), Abbvie Inc., USA),
   infliximab (REMICADE® (infliximab), MSD SHARP & DOHME GmbH, Germany),
   etanercept (ENBREL® (etanercept), Pfizer Inc., USA),
   certolizumab pegol (CIMZIA® (certolizumab pegol), UCB Pharma GmbH, Germany) or
   golimumab (SIMPONI® (golimumab), Janssen Biologics B.V., the Netherlands)
were added to human serum samples from normal donors (final concentration in the sample 0.8-25 mg/L).

To prepare calibrators,
   100 mg/L adalimumab (HUMIRAD (adalimumab)) or
   100 mg/L infliximab (REMICADE® (infliximab))

were added to a pool of human normal serum. Calibrators having lower inhibitor concentrations were generated by dilution with normal serum or a buffer solution.

The serum samples and the calibrator samples were diluted 1:5 and 1:20, respectively, with a buffer solution. 50 µL of serum sample or calibrator sample were mixed with 10 µL of REAGENT 1 and incubated at 37° C. for one minute. Then, 35 µL of REAGENT 2 were added to the mixture, and the light which is scattered at the antigen-antibody complex was measured within a period of 6 minutes at a wavelength of 840 nm in a nephelometric analyzer (BN II system, Siemens Healthcare Diagnostics Products GmbH, Germany). The measurement result ascertained is the change in the measurement signal (in bit) after 6 minutes.

Example 1a: Determination of Adalimumab with the Aid of an Adalimumab Calibration Curve Six serum calibrators having different adalimumab concentrations were measured using the method according to the invention and a calibration curve was prepared.

Furthermore, 14 serum samples having different adalimumab concentrations were measured using the method according to the invention. The adalimumab concentrations corresponding to the measurement results were read off on the previously prepared calibration curve.

Table 1 shows, for each sample, the adalimumab concentration to be expected according to adalimumab dosage (theoretical concentration) and the concentration ascertained in duplicate using the method according to the invention (measured concentration). It becomes apparent that the theoretical adalimumab concentrations are recovered with a maximum deviation of 0.44 mg/L in the concentration range of 0.8-3 mg/L and with a maximal deviation of 27.5% in the concentration range of 3-25 mg/L. This allows a precise quantification of adalimumab for therapy monitoring.

TABLE 1

| Adalimumab [mg/L], theoretical | Adalimumab [mg/L], measured (n = 2) |
|---|---|
| 25 | 18.1 |
| 22.5 | 16.5 |
| 20 | 15.3 |
| 17.5 | 13.5 |
| 15 | 12.3 |
| 12.5 | 9.8 |
| 10 | 8.0 |
| 7.5 | 6.1 |
| 5 | 3.7 |
| 3 | 2.6 |
| 2.5 | 2.1 |
| 2 | 1.9 |
| 1 | 1.1 |
| 0.8 | 0.9 |

Example 1b: Determination of Infliximab with the Aid of an Infliximab Calibration Curve Six serum calibrators having different infliximab concentrations were measured using the method according to the invention and a calibration curve was prepared.

Furthermore, 14 serum samples having different infliximab concentrations were measured using the method according to the invention. The infliximab concentrations corresponding to the measurement results were read off on the previously prepared calibration curve.

Table 2 shows, for each sample, the infliximab concentration to be expected according to infliximab dosage (theoretical concentration) and the concentration ascertained in duplicate using the method according to the invention (measured concentration). It becomes apparent that the theoretical infliximab concentrations are recovered with a maximum deviation of 0.47 mg/L in the concentration range of 0.8- mg/L and with a maximum deviation of 24.5% in the concentration range of 5-25 mg/L. This allows a precise quantification of infliximab for therapy monitoring.

TABLE 2

| Infliximab [mg/L], theoretical | Infliximab [mg/L], measured (n = 2) |
|---|---|
| 25 | 18.9 |
| 22.5 | 17.5 |
| 20 | 16.8 |
| 17.5 | 15.4 |
| 15 | 13.9 |
| 12.5 | 11.7 |
| 10 | 9.2 |
| 7.5 | 6.3 |
| 5 | 4.5 |
| 3 | 2.8 |
| 2.5 | 2.6 |
| 2 | 1.9 |
| 1 | 1.3 |
| 0.8 | 1.1 |

Example 1c: Determination of Various Therapeutic TNF-Alpha Inhibitors with the Aid of an Adalimumab Calibration Curve Six serum calibrators having different adalimumab concentrations were measured using the method according to the invention and a calibration curve was prepared.

Furthermore, 12 to 14 serum samples having different concentrations of adalimumab, infliximab, etanercept, certolizumab pegol or golimumab were in each case measured using the method according to the invention. The concentrations of adalimumab, infliximab, etanercept, certolizumab pegol or golimumab belonging to the measurement results were read off on the previously prepared calibration curve.

Tables 3 to 7 show, for each sample, the concentration to be expected according to dosage of the particular inhibitor (theoretical concentration) and the concentration ascertained in duplicate using the method according to the invention (measured concentration). It becomes apparent that, even without a corrective calculation, the theoretical concentrations of adalimumab and infliximab are recovered with a maximum deviation of 0.44 mg/L in the concentration range of 0.8-3 mg/L and with a maximum deviation of 42.3% in the concentration range of 3-25 mg/L (infliximab).

It was found that it is possible—when the measured concentration is plotted against the theoretical concentration—to calculate functions (linear or polynomial) which allow correction of the measured values, particularly for etanercept, certolizumab pegol and golimumab.

Using a linear function or a polynomial function (2nd or 3rd degree), the theoretical concentrations of adalimumab, infliximab, etanercept, certolizumab pegol and golimumab are recovered with acceptable deviations. It becomes apparent that the theoretical concentrations are recovered with a maximum deviation of 11.2% in the concentration range of 10-25 mg/L (golimumab). In the concentration range of 2-10 mg/L, the absolute deviations are maximally 0.61 mg/L (etanercept and infliximab).

For etanercept, a polynomial conversion is only possible in the concentration range of 2-25 mg/L.

TABLE 3

| Sample | Concentration, theoretical [mg/L] | Concentration, measured (n = 2) [mg/L] | Concentration, calculated, linear [mg/L] |
|---|---|---|---|
| Adalimumab | | | |
| 1 | 25 | 18.1 | 24.1 |
| 2 | 22.5 | 16.5 | 21.9 |
| 3 | 20 | 15.3 | 20.3 |
| 4 | 17.5 | 13.5 | 17.8 |
| 5 | 15 | 12.3 | 16.1 |
| 6 | 12.5 | 9.8 | 12.8 |
| 7 | 10 | 8.0 | 10.3 |
| 8 | 7.5 | 6.1 | 7.8 |
| 9 | 5 | 3.7 | 4.5 |
| 10 | 3 | 2.6 | 2.9 |
| 11 | 2.5 | 2.1 | 2.3 |
| 12 | 2 | 1.9 | 2.0 |
| 13 | 1 | 1.1 | 0.9 |
| 14 | 0.8 | 0.9 | 0.7 |

TABLE 4

| Sample | Concentration, theoretical [mg/L] | Concentration, measured (n = 2) [mg/L] | Concentration, calculated, polynomial [mg/L] |
|---|---|---|---|
| Infliximab | | | |
| 1 | 25 | 14.4 | 24.2 |
| 2 | 22.5 | 13.8 | 21.8 |
| 3 | 20 | 13.5 | 20.5 |
| 4 | 17.5 | 12.7 | 18.0 |
| 5 | 15 | 11.9 | 15.5 |
| 6 | 12.5 | 10.5 | 12.4 |
| 7 | 10 | 8.6 | 9.5 |
| 8 | 7.5 | 6.2 | 6.9 |
| 9 | 5 | 4.5 | 5.3 |
| 10 | 3 | 2.9 | 3.4 |
| 11 | 2.5 | 2.6 | 3.0 |
| 12 | 2 | 1.9 | 1.9 |
| 13 | 1 | 1.4 | 0.9 |
| 14 | 0.8 | 1.1 | 0.4 |

TABLE 5

| Sample | Concentration, theoretical [mg/L] | Concentration, measured (n = 2) [mg/L] | Concentration, calculated, polynomial [mg/L] |
|---|---|---|---|
| Etanercept | | | |
| 1 | 25 | 10.0 | 23.6 |
| 2 | 22.5 | 10.0 | 24.0 |
| 3 | 20 | 9.4 | 19.8 |
| 4 | 17.5 | 9.0 | 17.2 |
| 5 | 15 | 8.7 | 15.2 |
| 6 | 12.5 | 8.1 | 12.4 |
| 7 | 10 | 7.6 | 9.9 |
| 8 | 7.5 | 7.1 | 7.6 |
| 9 | 5 | 6.5 | 5.4 |
| 10 | 3 | 5.9 | 3.4 |
| 11 | 2.5 | 5.6 | 2.7 |
| 12 | 2 | 5.1 | 1.4 |

TABLE 6

| Sample | Concentration, theoretical [mg/L] | Concentration, measured (n = 2) [mg/L] | Concentration, calculated, polynomial [mg/L] |
|---|---|---|---|
| Certolizumab pegol | | | |
| 1 | 25 | 66.4* | 24.4* |
| 2 | 22.5 | 56.5* | 22.8* |
| 3 | 20 | 44.4* | 19.8* |
| 4 | 17.5 | 37.6* | 17.6* |
| 5 | 15 | 29.7* | 14.8* |
| 6 | 12.5 | 23.7* | 12.3* |
| 7 | 10 | 18.0* | 9.7* |
| 8 | 7.5 | 15.6* | 7.9* |
| 9 | 5 | 10.0 | 5.5 |
| 10 | 3 | 5.2 | 2.8 |
| 11 | 2.5 | 4.5 | 2.5 |
| 12 | 2 | 3.5 | 1.9 |
| 13 | 1 | 2.1 | 1.0 |
| 14 | 0.8 | 1.8 | 0.9 |

*= 1:20 sample dilution

TABLE 7

| Sample | Concentration, theoretical [mg/L] | Concentration, measured (n = 2) [mg/L] | Concentration, calculated, polynomial [mg/L] |
|---|---|---|---|
| Golimumab | | | |
| 1 | 25 | 18.0 | 23.7 |
| 2 | 22.5 | 17.5 | 21.7 |
| 3 | 20 | 17.3 | 21.1 |
| 4 | 17.5 | 16.2 | 17.1 |
| 5 | 15 | 16.1 | 16.7 |
| 6 | 12.5 | 14.8 | 13.0 |
| 7 | 10 | 13.3 | 10.0 |
| 8 | 7.5 | 11.3 | 7.2 |
| 9 | 5 | 7.7 | 4.7 |
| 10 | 3 | 4.8 | 3.3 |
| 11 | 2.5 | 3.8 | 2.7 |
| 12 | 2 | 3.2 | 2.2 |
| 13 | 1 | 1.9 | 1.0 |
| 14 | 0.8 | 1.6 | 0.6 |

The method described here allows the automatic determination of the concentrations of various TNF-alpha inhibitors in a single homogeneous assay.

Using a linear function or a polynomial function (2nd or 3rd degree) for converting the results obtained, the accuracy of the recovery of each individual TNF-alpha inhibitor is sufficient for therapy monitoring and therapy control.

The invention claimed is:

1. A method for quantitatively determining a therapeutic tumor necrosis factor (TNF)-alpha inhibitor in a sample, the method comprising the steps of:
   a) contacting the sample
      with isolated, free TNF-alpha protein to provide a reaction mixture;
   b) incubating the reaction mixture to allow binding of the isolated, free TNF-alpha protein to therapeutic TNF-alpha inhibitor in the sample;
   c) contacting the incubated reaction mixture with a first TNF-alpha binding partner to allow formation of a complex of isolated, free TNF-alpha protein remaining after step b) with the first TNF-alpha binding partner;
   d) determining the amount of the complex composed of TNF-alpha protein and the first TNF-alpha binding partner; and
   e) determining the amount of the therapeutic TNF-alpha inhibitor in the sample by comparing the amount of the complex composed of TNF-alpha protein and the first TNF-alpha binding partner determined in step d) with amounts of a complex composed of TNF-alpha protein and the first TNF-alpha binding partner in reaction mixtures containing samples having known concentrations of a TNF-alpha inhibitor.

2. The method as claimed in claim 1, wherein the first TNF-alpha binding partner is associated with a particulate solid phase and wherein the amount of the complex composed of TNF-alpha protein and the first TNF-alpha binding partner is determined by measuring the agglutination of the particulate solid phase.

3. The method as claimed in claim 2, wherein the agglutination of the particulate solid phase is measured photometrically.

4. The method as claimed in claim 2, wherein a first fraction of the particulate solid phase is associated with a first component of a signal-forming system and a second fraction of the particulate solid phase is associated with a second component of the signal-forming system and wherein the first component and the second component of the signal-forming system cooperate such that a detectable signal forms when the first component and the second component of the signal-forming system are brought into close proximity to one another and the agglutination of the particulate solid phase is measured on the basis of the signal formed.

5. The method as claimed in claim 4, wherein the first component of the signal-forming system is a chemiluminescent agent and the second component of the signal-forming system is a photosensitizer, or vice versa, and wherein the chemiluminescence is measured.

6. The method as claimed in claim 1, wherein the first TNF-alpha binding partner is associated with a solid phase and wherein the amount of the complex composed of TNF-alpha protein and the first TNF-alpha binding partner is determined in step d) by removing the solid phase and subsequently contacting the solid phase with a second TNF-alpha binding partner and measuring the amount of the second TNF-alpha binding partner which is bound to the complex which is associated with the solid phase and is composed of TNF-alpha protein and the first TNF-alpha binding partner.

7. The method as claimed in claim 6, wherein the second TNF-alpha binding partner is associated with a component of a signal-forming system.

8. The method as claimed in claim 6, comprising incubating the sample in step b) for a period of from 1 second to 10 minutes after contacting the sample with isolated, free TNF-alpha protein and before adding the first TNF-alpha binding partner.

9. The method as claimed in claim 6, wherein the first and/or the second TNF-alpha binding partner is an anti-TNF-alpha antibody.

* * * * *